Figure 1:
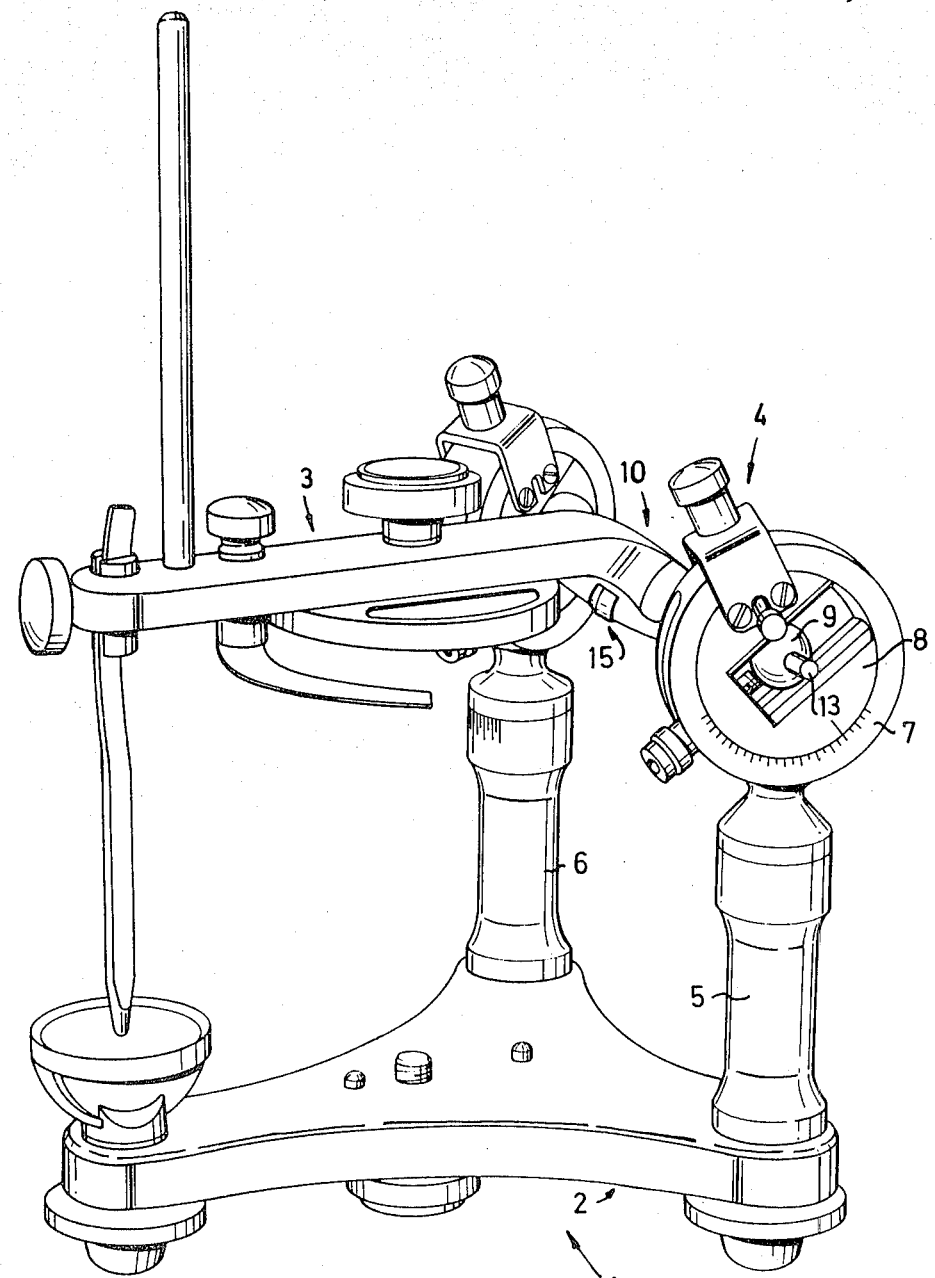

United States Patent [19]
Edwardson

[11] 4,439,150
[45] Mar. 27, 1984

[54] ARTICULATOR FOR USE IN MAKING DENTURES OR PARTS THEREOF
[75] Inventor: Svante R. Edwardson, Solna, Sweden
[73] Assignee: AB Dentatus, Hagersten, Sweden
[21] Appl. No.: 379,460
[22] Filed: May 18, 1982
[51] Int. Cl.³ .............................................. A61C 11/00
[52] U.S. Cl. ..................................................... 433/56
[58] Field of Search ............................. 433/56, 59, 54
[56] References Cited
U.S. PATENT DOCUMENTS
3,350,782 11/1967 Guichet ................................. 433/56
4,290,754 9/1981 Edwardson ........................... 433/56

Primary Examiner—Robert Peshock
Attorney, Agent, or Firm—Young & Thompson

[57] ABSTRACT

An articulator for use in making dentures or parts thereof comprises two principal members that are movably interconnected by means of a condylar mechanism. One of the principal members carries the condylar tracks of said mechanism while the other of said principal members carries the condylar shaft means of said mechanism. The condylar shaft means comprises adjustment means enabling simultaneous axial movement in opposite directions of two shaft members included in the condylar shaft means and each cooperating with a condylar ball. In this way the amount of axial play between the condylar shaft means and the condylar balls can easily be controlled.

4 Claims, 6 Drawing Figures

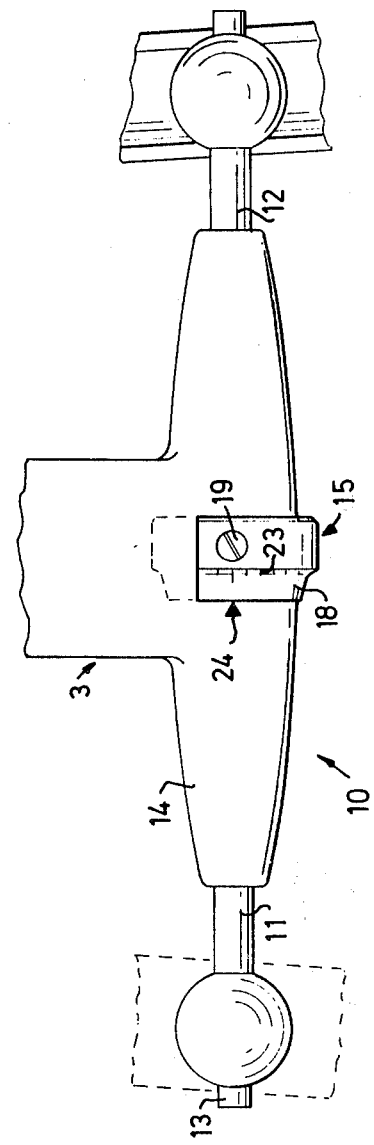
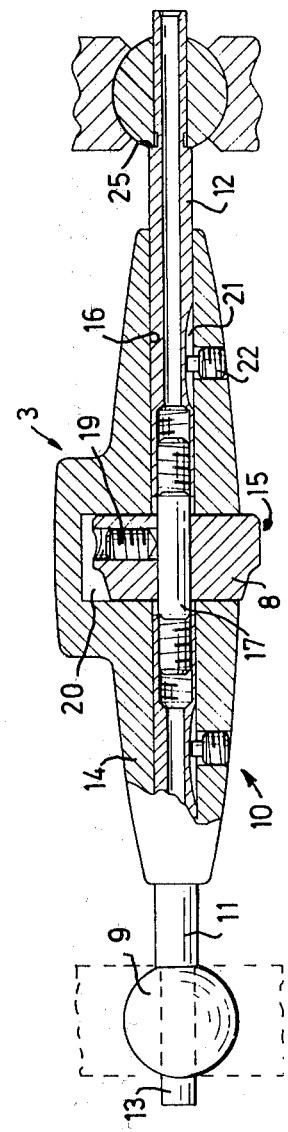

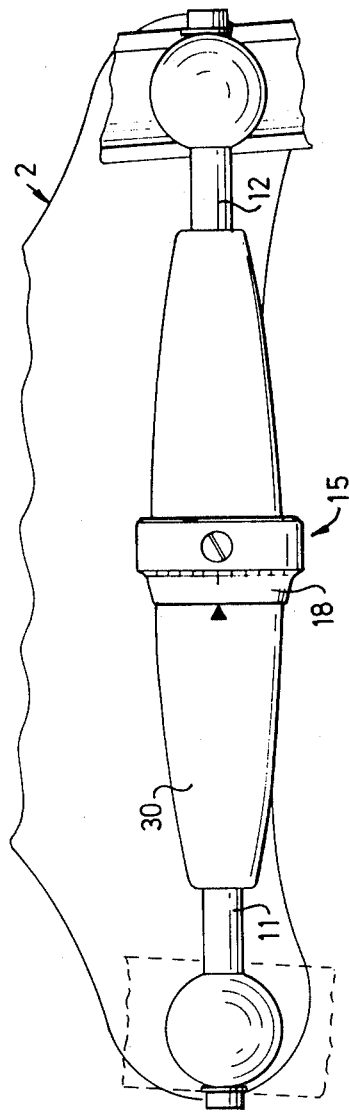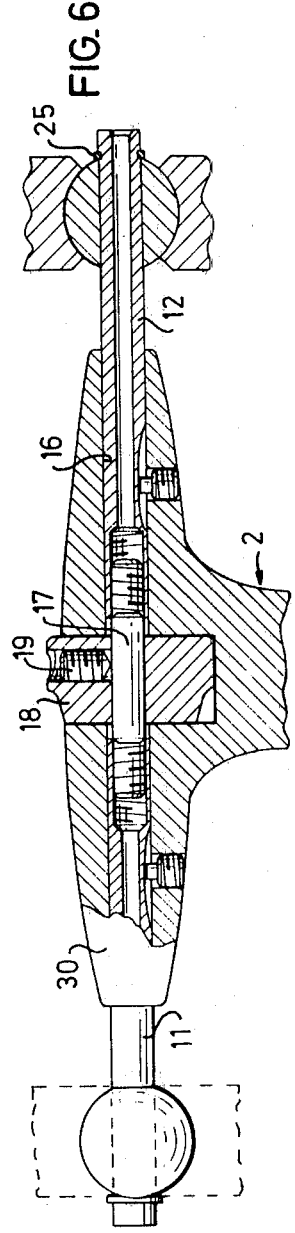

ARTICULATOR FOR USE IN MAKING DENTURES OR PARTS THEREOF

The present invention relates to an articulator, for use in making dentures or parts thereof, comprising a lower and an upper principal member which are interconnected by means of a condylar mechanism that allows relative movement between said principal members, one of said principal members being provided with condylar track members that are included in the condylar mechanism, the other of said principal members being provided with a condylar shaft means which comprises two shaft members, each of which has an end portion axially displaceably inserted into a bore in condylar ball that is mounted in one of said condylar track members, said shaft members being mutually movable in an axial direction and being interconnected by an intermediate part.

Numerous types of articulators for simulating a patient's bite and jaw movements are found on the market. Many of them are so-called average value articulators, the movement pattern of which is fixed, so as to simulate average jaw movements in the human species. Other types, however, allow various kinds of adjustment from individual records in order to facilitate a more accurate reproduction of the individual jaw movements. Especially there are types where the distance between the condylar balls can be set to different values. Common to all types is, however, that good function requires that the lateral play in centric relation for the upper principal member is kept to a minimum. To this end it is known to make the position of the shaft members cooperating with the condylar balls adjustable in order to allow elimination of lateral play.

Examples of such adjustability are disclosed in U.S. Pat. No. 4,290,754. According to said prior art it is necessary, in order to change the distance between the shaft members, to first use a special tool to loosen a stop screw before one of the shaft members can be moved. Having made the desired movement, the screw has to be tightened again. Then the same procedure has to be repeated for the other shaft member. Care has to be taken so as to obtain equal displacement of both shaft members. Adjustment thus becomes time consuming and might not always be accurate.

The object of the invention is to eliminate said drawbacks and to provide an improved articulator of the kind indicated which is more easy to adjust and which is simple.

Said object is achieved, according to the invention, by providing an articulator where the condylar shaft means comprises adjustment means enabling simultaneous axial movement of said shaft members in opposite directions.

Very easy adjustment becomes possible when said adjustment means comprises a rotatable wheel means which is axially fixed in an opening in said one principal member, and which is rotatable together with the intermediate part to displace said shaft members. This eliminates the need for special adjustment tools and also guarantees that symmetrical displacement of the shaft members can be obtained.

An articulator made according to the invention can either be of the kind in which the upper principal member is provided with the condylar shaft means, or of the kind in which the lower principal member is provided with the condylar shaft means. Both these kinds of articulators are marketed by AB Dentatus, Hägersten, Sweden.

The following is a description, by way of example only, of embodiments of the invention, reference being made to the accompanying drawings, in which:

FIG. 1 shows a perspective view of a first embodiment of an articulator according to the invention.

Figure 4:
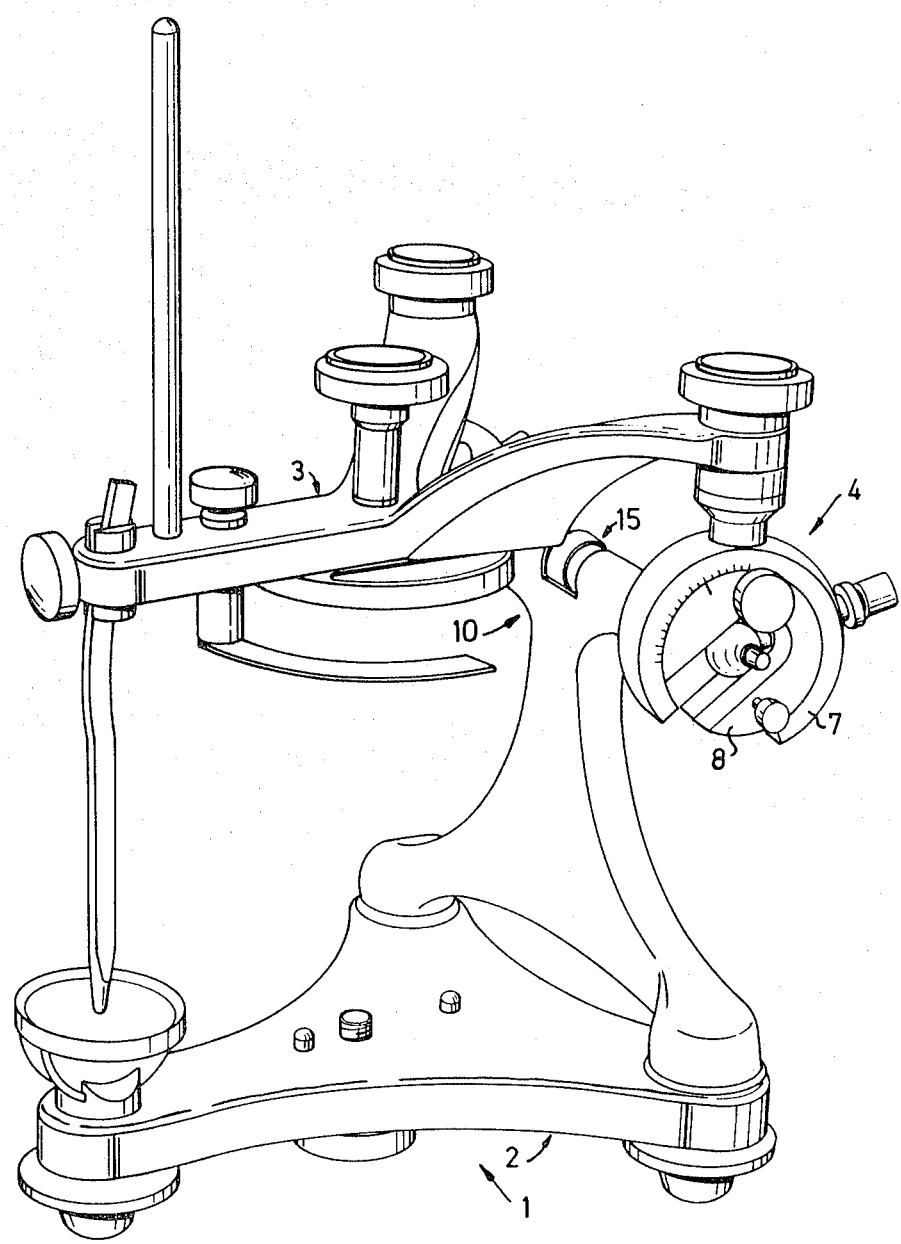

FIG. 2 shows a top view of a portion of the upper principal member of the embodiment in FIG. 1, FIG. 3 shows an end view, partly in section, of the member in FIG. 2, FIG. 4 shows a perspective view of a second embodiment of an articulator according to the invention, FIG. 5 shows a top view of a portion of the lower principal member of the embodiment in FIG. 4, and FIG. 6 shows an end view, partly in section, of the member in FIG. 5.

As can be seen from FIG. 1 an articulator 1 according to the invention comprises a lower principal member 2, which serves as a stand, and an upper principal member 3. The principal members 2 and 3 are interconnected by a condylar mechanism 4 that allows relative movement between said principal members 2 and 3 in order to simulate the movements of the jaw joint. The lower principal member 2 is provided with condylar posts 5 and 6, each adjustably supporting a holder 7 in which a condylar track member 8 is adjustably mounted and holds a condylar ball 9.

The upper principal member 3 is, as is more clearly seen in FIG. 2 and FIG. 3, provided with a condylar shaft means 10 that comprises two shaft members 11 and 12, each of which has an end portion 13 that is inserted into a bore in the corresponding condylar ball 9, thus allowing pivotal movement of the upper principal member 3 in a manner well known within the art.

As seen in FIG. 2 the condylar shaft means 10 is supported by a longitudinal portion 14 of the upper principal member 3 and is provided with an adjustment means 15 the purpose of which is to allow easy control of the axial distance between the two shaft members 11 and 12.

Referring now specifically to FIG. 3, it will be seen that the longitudinal portion 14 is provided with an axial through-bore 16 into which said shaft members 11 and 12 are slidably inserted from opposite ends. One end of the shaft member 11 is in threaded engagement with one end of an intermediate, pin-like part 17 located within the bore 16. The other end of said intermediate part 17 is in threaded engagement with the adjacent end of the other shaft member 12. Between its two ends the intermediate part 17 carries a wheel 18 which is secured to the intermediate part 17 by means of a stop screw 19, all these parts being included in the adjustment means 15. The wheel 18 is located in an opening 20 in the longitudinal portion 14 and is accessible for rotation by an operator. In order to prevent rotation of the shaft members 11 and 12 each of them is provided with an axial groove 21 which cooperates with a guide member 22 removably mounted in the longitudinal portion 14. The threads at the two ends of the intermediate part 17 have oppositie directions, thus allowing the shaft members 11 and 12 to move in opposite directions axially when rotating the wheel 18 in a certain direction. On each of the shaft members 11 and 12 there is provided a stop means 25, e.g. a shoulder, for seating against the side of the respective condylar ball facing the wheel 18. Elimination of lateral play thus requires the shaft members 11 and 12 to be moved apart.

As can be seen in FIG. 2 the wheel 18 is provided with index means 23 cooperating with an index mark 24 on the longitudinal portion 14. Said index means preferably indicates the change in distance between the shaft members 11 and 12 resulting from a certain rotation of the wheel 18. By making the wheel 18 fit rather tightly in the opening 20 axial play of the wheel 18 and thus of the shaft members 11 and 12 can be minimized. In addition, a certain locking action for the wheel 18 can be obtained, thus reducing the risk of nonintentional rotation of the wheel 18.

In the alternative embodiment of the articulator disclosed in FIGS. 4–6 the main difference from the embodiment disclosed in FIGS. 1–3 is that the condylar shaft means 10 is carried by a longitudinal portion 30 of the lower principal member 2 while the condylar track members 8 and their holders 7 are carried by the upper principal member 3. Another difference is that each of the stop means 25, e.g. a lock ring seated in a groove in the shaft member, is intended for seating against the side of the respecitve condylar ball facing away from the wheel 18. Thus, elimination of lateral play requires the shaft members 11 and 12 to be moved towards each other. Depending on the hand of the threads used, the wheel 18 can be rotated in the same or opposite direction as with the embodiments of FIGS. 1–3 in order to eliminate lateral play. Obviously, the size of the thread pitch used influences the size of the axial displacement of the shaft members obtained for a certain rotation of the wheel 18. A small pitch allows very accurate control of the shaft members, while a large pitch provides less accurate control.

Since articulators are well known it is not considered necessary to go into further detail as regards the featurs normally found on articulators and the normal operation of articulators.

With an articulator according to the invention it becomes very easy to eliminate lateral play for the upper principal member, i.e. to obtain positive centric position, by simply turning the wheel 18 to a position where the stop means 25 on the shaft members 11 and 12 are firmly seated against the condylar balls.

Another advantage is that by turning the wheel 18 in the proper direction a certain lateral play can be obtained, thus allowing the principal upper member to be moved sideways a certain distance in either direction for testing the effect of a certain shift. Having tested such side shift resetting is done by turning the wheel 18 back to the original setting.

The common Bennett setting of the condylar track members normally makes it complicated to test a forward movement of the upper principal member once lateral play has been eliminated in centric relation. With the invention, however, such forward movement becomes easy once stop screws at the condylar track members have been loosened and the wheel 18 has been turned in the proper direction for allowing a variation in distance between the condylar balls caused by the Bennett setting at such forward movement.

The wheel 18 can be made to conform well to the general shape of the principal member on which it is located, and therefore can be made to have almost no negative influence on accessibility on a workpiece mounted in the articulator. It will be observed that a permanent side shift for the upper principal member can be obtained by loosening the stop screw 19, displacing the intermediate part 17 a required distance relative to the wheel 18, and tightening the stop screw again. Alternatively, the shaft members 11 and 12 can be rotated a required number of turns after loosening the guide members 22 to allow rotation of the shaft members.

What I claim is:

1. An articulator, for use in making dentures or parts thereof, comprising a lower and an upper principal member which are interconnected by means of a condylar mechanism that allows relative movement between said principal members, one of said principal members being provided with condylar track members that are included in said condylar mechanism, the other of said principal members being provided with a condylar shaft means which comprises two shaft members, each of which has an end portion axially displaceably inserted into a bore in a condylar ball that is mounted in one of said condylar track members, said two shaft members being mutually movable in an axial direction and being interconnected by an intermediate part, characterized in that said condylar shaft means comprises adjustment means enabling simultaneous axial movement of said shaft members in opposite directions, said adjustment means comprising a rotatable wheel means which is held axially fixed in an opening in said one principal member, and which is rotatable together with the intermediate part to displace said shaft members, each of said shaft members being non-rotatably mounted in said one principal member and being in threaded engagement with said intermediate part, which has two oppositely directed threads, one for each shaft member.

2. An articulator as claimed in claim 1, in which said rotatable wheel means is provided with index means around at least a portion of its periphery, for indicating the amount of axial displacement between said shaft members resulting from a certain rotation of the wheel, there being provided on said one principal member an index mark associated with said index means.

3. An articulator as claimed in claim 1, in which said upper principal member is provided with said condylar shaft means.

4. An articulator as claimed in claim 1, in which said lower principal member is provided with said condylar shaft means.

* * * * *